United States Patent [19]

Mächler et al.

[11] Patent Number: 4,655,555
[45] Date of Patent: Apr. 7, 1987

[54] OBJECTIVE WITH ASPHERIC SURFACES FOR IMAGING MICROZONES

[75] Inventors: Meinrad Mächler, Ellwangen; Franz Glück; Harry Schlemmer, both of Aalen; Reinhold Bittner, Mögglingen, all of Fed. Rep. of Germany

[73] Assignee: Carl-Zeiss-Stiftung, Heidenheim, Fed. Rep. of Germany

[21] Appl. No.: 675,735

[22] Filed: Nov. 28, 1984

[30] Foreign Application Priority Data

Dec. 3, 1983 [DE] Fed. Rep. of Germany ....... 3343868

[51] Int. Cl.⁴ .............................................. G02B 13/18
[52] U.S. Cl. .................................... 350/432; 350/504; 350/619
[58] Field of Search ................ 350/432, 619, 504, 435

[56] References Cited

U.S. PATENT DOCUMENTS 804,996 11/1905 Anthony ............................. 350/504

FOREIGN PATENT DOCUMENTS 0501294 7/1930 Fed. Rep. of Germany ...... 350/504
0141613 9/1982 Japan ................................... 350/619

OTHER PUBLICATIONS

Glass, "Angle-Amplifying Optics", 10/1975, Laser Report Annual Report, 1974, UCRL-50021-74, pp. 238-239.

*Primary Examiner*—John K. Corbin
*Assistant Examiner*—Rebecca D. Gass
*Attorney, Agent, or Firm*—Walter Ottesen

[57] ABSTRACT

The invention is directed to objectives for imaging small regions with a large aperture angle. The objectives include two aspheric bodies made of optically isotropic material wherein the deflection of the light rays is achieved by total reflection on the outer surfaces. The light entry surfaces and light exit surfaces are configured as spherical surfaces having center points at least approximately coincident with the focal points of the aspheric bodies.

15 Claims, 13 Drawing Figures

OBJECTIVE WITH ASPHERIC SURFACES FOR IMAGING MICROZONES

FIELD OF THE INVENTION

The invention relates to an objective having reflecting aspheric surfaces. The area of application is preferably with respect to spectrometers such as simultaneous spectrometers having diode arrays or the like. The catoptric objective of the invention is, however, also suited for application to other areas where microzones with larger apertures are imaged.

BACKGROUND OF THE INVENTION

Simultaneous spectrometers with diode arrays have become known in the past few years with respect to numerous areas of application. In this connection, reference may be made to the following: GIT Fachzeitschrift Lab., Book 3, 1983, page 170; Markt & Technik, Number 49, Dec. 4, 1981, page 52; brochure of Carl Zeiss W 90-100-d; and, brochure of Hewlett Packard, Number 23-5953-8032 GE. The essential advantages of these spectrometers are their very compact configuration and the speed with which an entire spectrum is measured.

A diode-array spectrometer is disclosed in published German patent application DE-OS No. 32 15 879 wherein the spectra measurements in the blood stream are made possible with a light conductor probe. In this application, the spectrometer has an aperture ratio which accepts the aperture of the light conductor without reduction. It is advantageous to make the aperture ratio large also for spectrometers having an integrated sample compartment for energetic reasons. This is possible by utilizing holographic concave gratings; however, for the sample compartment, an imaging optic for the same large aperture ratio is required. This imaging optic should be suitable for the entire spectral range of 200 to 1100 nm which is of interest whereby the imaging of small regions or so-called microzones is sufficient because of the small dimensions of the receiving surfaces of the diode-arrays. In most cases, an imaging ratio of almost or exactly 1:1 is appropriate. The energy losses because of reflection on the boundary surfaces should be as small as possible for the entire spectral range.

There are numerous objectives known in the area of microscopy which have a large aperture ratio. However, these objectives have only a limited wavelength range. Furthermore, they are configured for large magnification. Conventional objectives must be made of many components for a wavelength range up to 200 nm and are therefore expensive and have a low transmission factor.

Catoptric objectives are also known from microscopy wherein the ray path between the two mirrors runs in a solid transmitting body such as glass, quartz or the like. This transmitting body has entry and exit surfaces concentric to the object or image location so that the position of the image location is independent of the wavelength which is used. With respect to these catoptric objectives, reference may be made to "Jenaer Jahrbuch", 1956, page 30. The disadvantage of these catoptric objectives is that they are not suitable for very large apertures if the object lies in space and that they have a relatively large diameter and above all, that the reflective losses on the rear side of the mirrored glass surfaces are especially large in the ultraviolet range.

A catoptric objective is disclosed in an article entitled "Aspheric Potpourri" by Lawrence Mertz which was published in Applied Optics, Volume 20, 1981, pages 1127 to 1131. This catoptric objective is made up of two ellipsoidal-shaped hollow bodies having focal points on the optical axis whereby the inner focal points are coincident. If the ellipsoids are the same size, the imaging is in the ratio of 1:1 and is aplanatic. A microscope objective made of two rotationally symmetrical hollow bodies is disclosed in a further article of Lawrence Mertz entitled "Geometrical Design for Aspheric Reflecting Systems" published in Applied Optics, Volume 18, 1979, pages 4182 to 4186. This microscope objective has a 10-power enlargement capacity. If the system is aplanatic as indicated, then it should not be considered to be a double ellipsoidal system which is made manifest by the bearly visible ray traces in FIG. 10 of the article. The double systems described with aspheric inner surfaces have the disadvantages that: the aspheric inner surfaces are very difficult to produce; with reflections at these inner surfaces intense polarization occurs especially with large angles of incidence; relatively large reflection losses occur; and, the necessary masking of the inner aperture is associated with mechanical complexity.

SUMMARY OF THE INVENTION

It is therefore an object of the invention to provide an objective which can image with a large aperture angle a small region at a ratio of nearly or equal to 1:1 with minimal errors while at the same time providing the greatest possible transmittance in the entire wavelength range of 200 to 1100 nm.

The object of the invention is achieved with a catoptric objective having reflecting aspheric surfaces wherein the reflecting aspheric surfaces are outer surfaces of optic isotropic aspheric bodies and the light entry and light exit surfaces of the aspheric bodies are configured as spherical surfaces having center points at least approximately coincident with the focal points of the aspheric bodies.

The aspheric surfaces are configured as outer surfaces of optically isotropic aspheric bodies thereby causing total reflection at the aspheric surfaces so that very low losses occur and a large transmittance is obtained. With this configuration, the outer surfaces do not require any coating because of the air which bounds these surfaces and this is made possible because the aspheric bodies can be held outside of the optically effective outer surfaces. The aspheric bodies can be made, for example, from fluorite or fused quartz for the required wavelength range of 200 to 1100 nm.

In a preferred embodiment of the invention, both aspheric bodies are ellipsoids having focal points arranged on a single axis and with the inner focal points being at least approximately disposed at a single point.

If both ellipsoids have the same numerical eccentricity, the imaging ratio is 1:1 and the image formation of the one outer focal point in the other outer focal point is aplanatic. A good image formation is also obtained for small regions about the outer focal points in the planes perpendicular to the optical axis. With an imaging ratio of 1:1, the inner focal points are located at a single point. For other imaging ratios, the inner focal points can be placed somewhat apart from each other in order to facilitate the correction of imaging errors as will be shown later.

In a further advantageous embodiment of the invention, the aspheric bodies are an ellipsoid and a paraboloid having respective focal points on one axis whereby the focal point of the paraboloid is coincident with a focal point of the ellipsoid. In this arrangement, the center point of the outer spherical surface of the paraboloid is at infinity or, stated otherwise, the outer boundary surface of the paraboloid is planar.

Because of manufacturing reasons, it can be advantageous if the two aspheric bodies are not made from a single piece. However, if a compact configuration is nonetheless useful, the two bodies can be produced separately and cemented together or wrung together in optical contact.

The two aspheric bodies can also be separated by a spherical air gap having a center point at least approximately coincident with the inner focal points of the aspheric bodies.

In a further advantageous embodiment of the invention, a sphere made of optically isotropic material can be disposed between the two aspheric bodies and have a center point at least approximately coincident with the inner focal points of the aspheric bodies.

It is especially advantageous to make the sphere from a material having a refractive index larger than the refractive index of the aspheric body. The sphere can be made, for example, from sapphire. With this kind of a sphere, the points of an object plane perpendicular to the optical axis and passing near or through an outer focal point can be imaged with a substantially smaller circle of least confusion and with a smaller field curvature than would be the case with a homogeneous union of the ellipsoids.

In another advantageous embodiment of the invention, the aspheric bodies can be two paraboloidal portions having axes inclined to the optical axis of the imaging system whereby the center points of the outer spherical surfaces are also the focal points of the paraboloidal portions. The center points of the inner spherical surfaces lie at infinity and an even number of planar mirrors is arranged between the paraboloidal portions so that a parallel bundle of rays which enters and exits from the planar mirror system intersects itself. With an arrangement of the reflecting planar mirrors of this kind, the total system has good imaging characteristics.

In a further embodiment of the invention, at least a part of the planar mirrors is coated with filter layers. Since these filter layers lie in the telecentric part of the path of the rays, very narrow band interference multilayer filters also can be utilized.

A special advantage of the aspherical surfaces utilized when compared to other aspherical surfaces is that they can be optically tested with a relatively simple procedure also during the production process.

A further advantage of the objective made of two ellipsoids is that the position of the objective between the object plane and image plane is within wide limits freely selectable because the imaging ratio is only influenced by the ratio of the numerical eccentricities and therefore the points of intersection are still in large measure freely selectable because of the size of the ellipsoids.

BRIEF DESCRIPTION OF THE DRAWING

The invention will now be described with reference to the drawing wherein:

FIG. 8a is an example of the application of an objective in the sample compartment of a fluorescence spectrometer; and, FIG. 8b is an example of the application of two different objectives in the sample compartment of a Raman spectrometer.

DESCRIPTION OF THE PREFERRED EMBODIMENTS OF THE INVENTION

Figure 1:
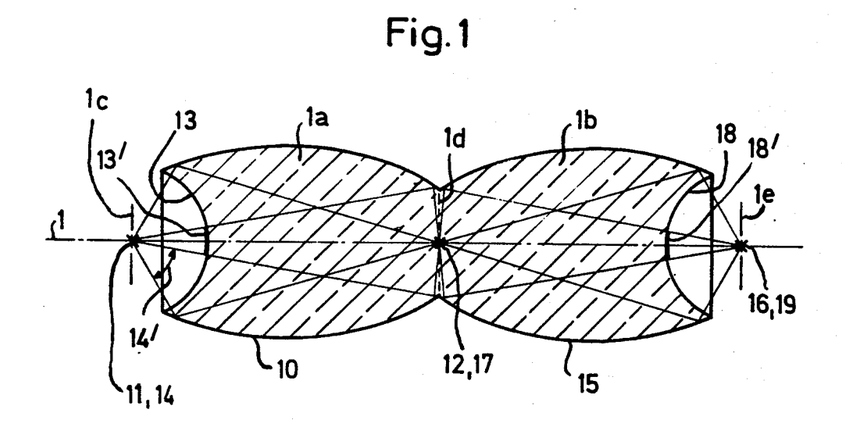
FIG. 1 is an objective made of two identical ellipsoids.

The objective shown in FIG. 1 has an imaging ratio of 1:1. It includes two ellipsoids 1a and 1b which both have the same dimensions and are made of an optically isotropic material. The focal points 11 and 12 as well as 16 and 17 lie on a common axis 1. The ellipsoids are so arranged with respect to one another that the focal point 12 of the ellipsoid 1a is coincident with the focal point 17 of the ellipsoid 1b. The outer end faces 13 and 18 are configured as spherical dishes having respective centers 14 and 19. The center point 14 of the spherical dish 13 is coincident with the focal point 11 of the ellipsoid 1a and the center point 19 of the spherical surface 18 is coincident with the focal point 16 of ellipsoid 1b for an imaging ratio of 1:1 in the illustrated embodiment.

The object plane 1c is perpendicular to axis 1 and passes through points 11, 14; whereas, the image plane 1e is perpendicular to the axis 1 and passes through the points 16, 19. It is clear that the focal point 11 is exactly imaged in the focal point 12, 17 by the elliptical outer surface 10 and that the focal point 12, 17 is exactly imaged in the focal point 16 by the elliptical outer surface 15. In contrast, a point lying in the object plane 1c at any desired point near the focal point 11 is not imaged as a point in the intermediate plane 1d since the rays reflected from the various zones of the elliptical outer surface 10 meet the intermediate plane 1d at different locations. However, this zone error is compensated by the second ellipsoid 1b which has the same dimensions as the ellipsoid 1a for a point located not too far from the axis 1 so that the rays in the image plane 1e again intersect practically at one point. The occurring deviations become especially noticeable in an image field curvature. This matter will be treated in greater detail in the discussion referring to FIGS. 5a and 5b.

It is understood that no rays from the image plane 1c are permitted to reach object plane 1e without reflections on the elliptical outer surfaces because they do not contribute to imaging; instead, they would contribute to a reduction in contrast. For this reason, a mask 13' is provided on the spherical surface 13 and can be applied, for example, by vaporization. The mask 13' masks the inner aperture so that only the outer annular aperture 14' is utilized. The mask 18' shields stray light which can develop within the two ellipsoids 1a and 1b.

The reflections on the two elliptical outer surfaces 10 and 15 occur within the entire range by total reflection. This not only has the advantage that deposited reflecting layers can be dispensed with but also that practically no losses occur and this within the entire wavelength range. Furthermore, a polarization of the rays is virtually prevented. For this, care must be only taken that, within the utilized regions of the outer surfaces 10 and 15, only air bounds the surfaces. The ellipsoids 1a and 1b can be therefore held outside of the optically utilized regions.

Figure 2:
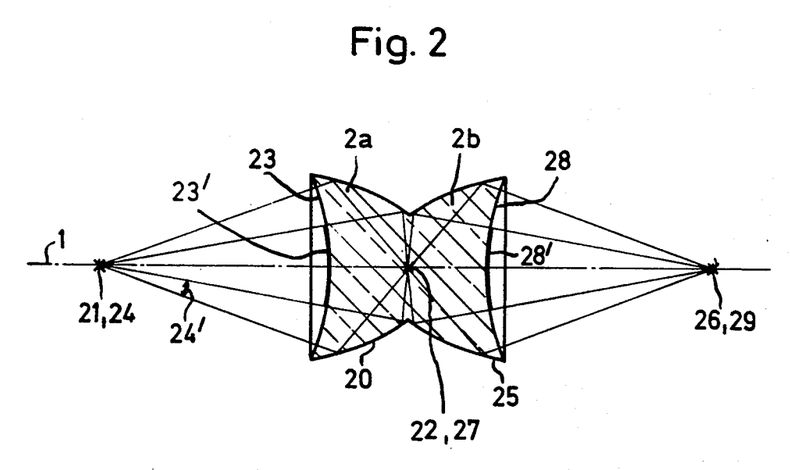
FIG. 2 is another objective made of two identical ellipsoids.

FIG. 2 shows a further objective wherein the imaging ratio is 1:1 with a smaller aperture and therefore greater intersection lengths. The ellipsoids are identified by reference numerals 2a and 2b and the outer surfaces thereof with reference numerals 20 and 25. All focal points lie on the axis 1 whereby the inner focal point 22 of the ellipsoid 2a is coincident with the inner focal point 27 of ellipsoid 2b. The outer focal point 21 is coincident with the center point 24 of the concentric spherical surface 23 and the outer focal point 26 is coincident with the center point 29 of the spherical surface 28. Reference numerals 23' and 28' identify masks for the inner aperture and reference numeral 24' identifies the outer annular aperture which is utilized.

Figure 3:
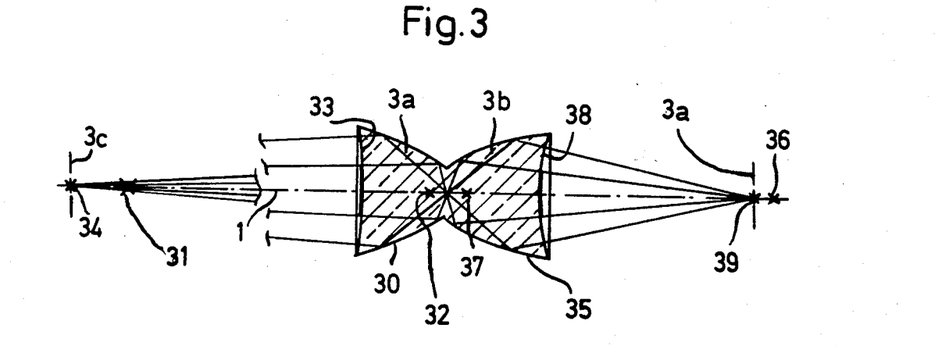
FIG. 3 is an objective made of two different ellipsoids having an imaging ratio of 3:1.

In FIG. 3, an objective having an imaging ratio of 3:1 is illustrated. It is made up of the ellipsoids 3a and 3b having respective outer surfaces 30 and 35. The system is no longer aplanatic because the imaging ratio deviates from 1:1. It is therefore advantageous for the imaging characteristics not to have focal point 32 of ellipsoid 3a coincident with the focal point 37 of the ellipsoid 3b. The spacing of the focal points 32 and 37 is greatly exaggerated in FIG. 3 for the purposes of illustration. In actuality, the spacing is in the order of magnitude of micrometers. The spacings between the object and image planes or between the center points of the spherical surfaces and the focal points corresponding thereto are substantially greater. Between the object plane 3c which passes through the center point 34 of the spherical surface 33 and the outer focal point 31 of ellipsoid 3a, the spacing is several millimeters. Between the imaging plane 3e which passes through the center point 39 of the spherical surface 38 and the outer focal point 36 of ellipsoid 3b, the spacing can be approximately 0.5 mm for the system shown in FIG. 3 for a ratio of 1:1. More precise data will follow after an explanation of FIGS. 5a to 5c. The object plane and image plane of FIG. 3 can of course be exchanged with one another.

Figure 4A:
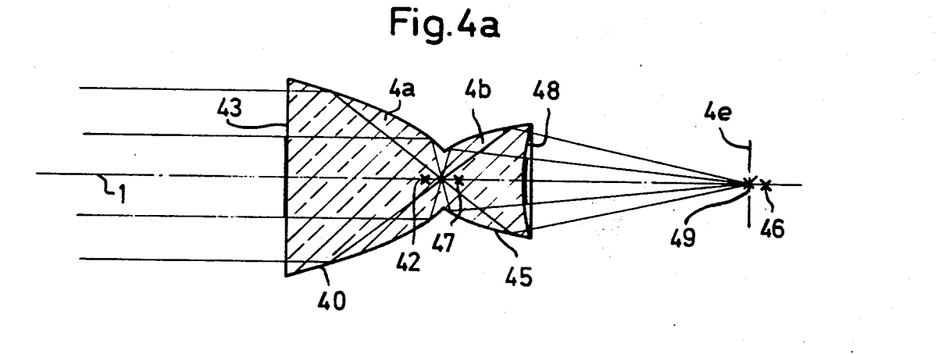
FIG. 4a is an objective made up of two ellipsoids for imaging from or to infinity.

FIG. 4a illustrates an objective for imaging to or from infinity. This objective is made up of ellipsoids 4a and 4b having respective outer surfaces 40 and 45. In this embodiment too, it is advantageous for the imaging characteristics if the inner focal points 42 and 47 of the respective ellipsoids are not coincident and if the imaging plane 4e, which passes through the center point 49 of the spherical surface 48, does not pass through the outer focal point 46. The outer spherical surface 43 of the ellipsoid 4a has practically an infinitely large radius and is therefore practically planar.

Figure 4B:
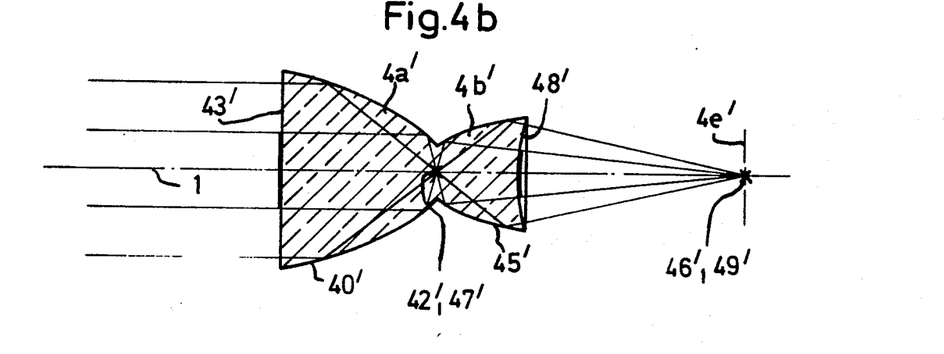
FIG. 4b is an objective made up of an ellipsoid and a paraboloid for imaging from or to infinity.

FIG. 4b illustrates a combination of a paraboloid 4a' having outer surface 40' and an ellipsoid 4b' having an outer surface 45'. With this embodiment, imaging to or from infinity is also possible. In this case, the focal point 42' of the paraboloid 4a' should be made coincident with the inner focal point 47' of the ellipsoid 4b' and the image plane 4e' which passes through center point 49' of spherical surface 48' should pass through the outer focal point 46' of ellipsoid 4b'. The combination shown in FIG. 4b of paraboloid 4a' and ellipsoid 4b' has the disadvantage with respect to the combination of ellipsoids 4a and 4b illustrated in FIG. 4a that it has larger imaging errors and is very sensitive to adjustment.

Figure 5A:
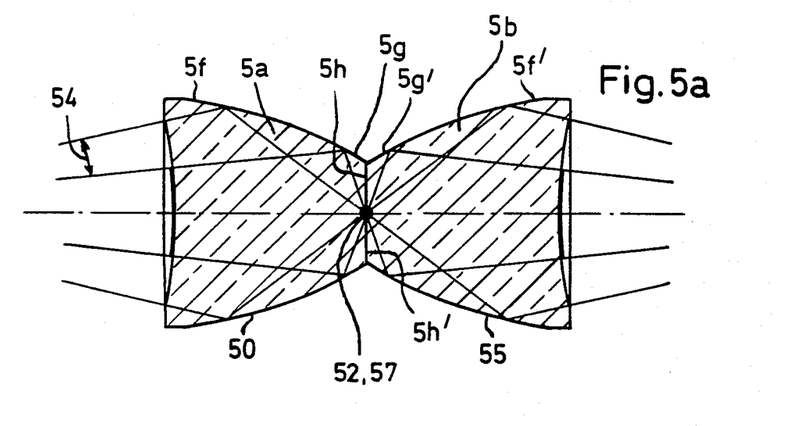
FIG. 5a is an objective made up of two ellipsoids which have been wrung together.

With respect to the embodiments shown in FIGS. 1 to 4, the outer surfaces such as those identified by reference numerals 10, 15 or 40', 45' are so drawn that they pass directly one into the other. Production of aspheric surfaces of this kind is made simpler if these surfaces would have regions at their forward and rearward ends which are not optically utilized and would therefore not have to correspond precisely to each other. For this reason, the ellipsoids 5a and 5b in FIGS. 5a to 5c have regions 5f and 5f' at the outer ends thereof which are outside of the regions used by the outer aperture 54 on the outer surfaces 50 and 55 which can be made as large as is advantageous for producing and holding the ellipsoids. The regions 5g and 5g' on the inner ends can first likewise be made so large as is required for producing the outer surface in the region which is optically utilized. In a further production step, the ellipsoids 5a and 5b receive planar surfaces 5h and 5h' as shown in FIG. 5a. These planar surfaces 5h and 5h' pass through focal points 52 and 57 when the completed ellipsoids are wrung onto each other. On the other hand, if the ellipsoids are cemented to each other, then the planar surfaces 5h and 5h' are processed so that they are correspondingly deeper.

Figure 5B:
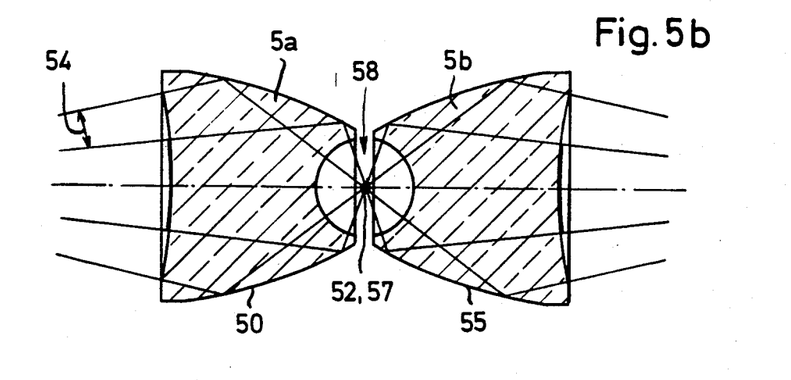
FIG. 5b is an objective having an intermediate air gap of spherical shape.

FIG. 5b shows another embodiment for the transition between the two ellipsoids 5a and 5b. In this embodiment, there is no direct union between the ellipsoids; instead, the transition is achieved with an intermediate spherically-shaped air gap 58. The center point of the air gap 58 is coincident with the two inner focal points 52 and 57 of the ellipsoids 5a and 5b so that all rays which pass through these focal points are not deflected.

Figure 5C:
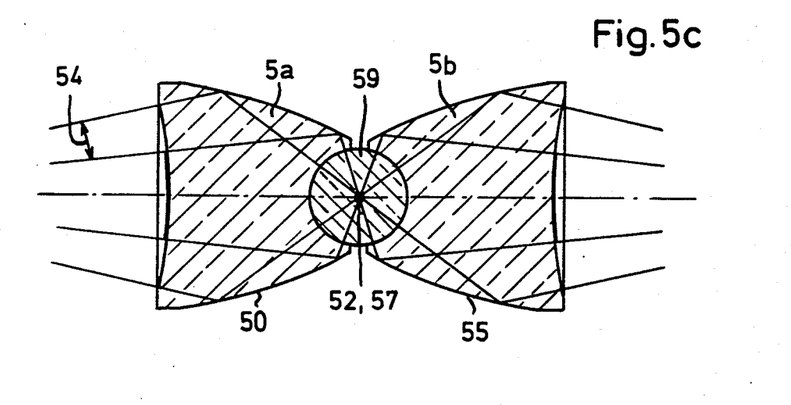
FIG. 5c is an objective wherein a sphere is placed between the aspheric bodies.

An advantageous embodiment for the transition between the two ellipsoids 5a and 5b is shown in FIG. 5c. Here the union between the two ellipsoids is achieved with a glass sphere 59 having a center point which is likewise coincident with the two inner focal points 52 and 57. It is especially advantageous to make the sphere from a material having a large refractive index such as sapphire thereby making the imaging errors for points outside of the focal points especially small. This is especially the case for image field curvature which can be reduced by a factor of 6 when compared to the air sphere and by a factor of 2.3 when compared to a connection made of a material having the same refractive index.

For an imaging ratio of 1:1, the embodiment shown in FIG. 5c can be made pursuant to the following data:
 major semiaxis of the ellipsoids: 34.93 mm
 minor semiaxis of the ellipsoids: 12.81 mm
 numerical eccentricity: 0.93032605
 spacing of outer focal points: 129.985 mm
 radius of outer spherical surfaces: 45.316 mm
 radius of inner spherical surfaces: 4.732 mm
 center thickness of the ellipsoids: 14.945 mm aperture angle: 12.5°
material of the ellipsoids: Suprasil
material of the sphere: sapphire With this objective, an object point lying in the object plane at a spacing of 1 mm from the focal point, the deviation from the image plane caused by image field curvature amounts to 0.15 mm. Two objectives with these data are utilized for the beam path described in FIG. 7 for a spectrometer.

Figure 6A:
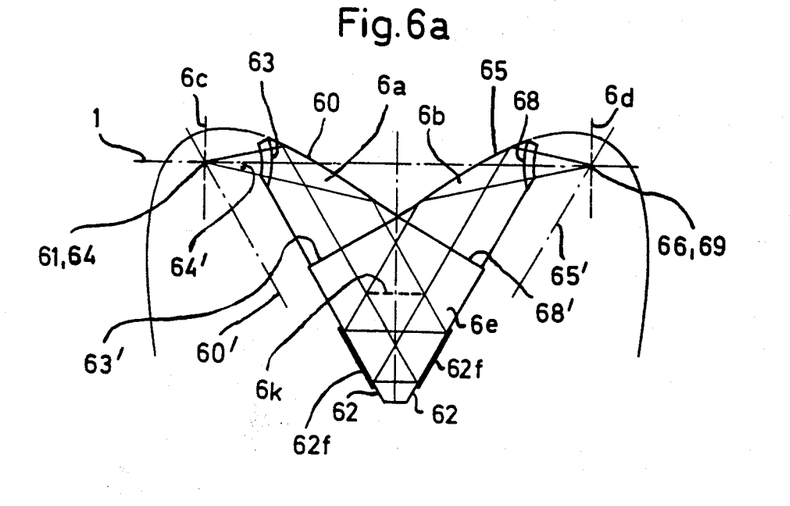
FIG. 6a is an objective made of two paraboloids having two reflecting surfaces between the paraboloids.
Figure 6B:
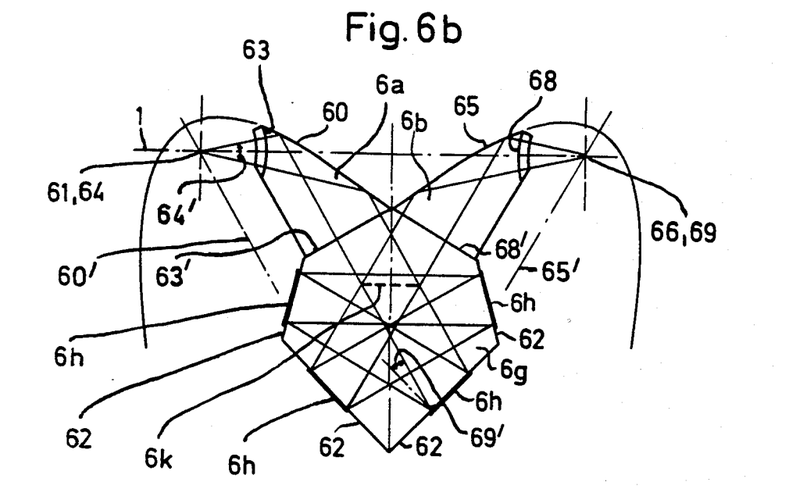
FIG. 6b is an objective made of two paraboloids with four reflecting surfaces between the paraboloids.

The objective illustrated in FIG. 3 for an imaging ratio of 3:1 can be configured pursuant to the following data whereby a sapphire sphere corresponding to FIG. 5c is placed between the two ellipsoids:

major semiaxis of the ellipsoid 3a: 99.454 mm
minor semiaxis of the ellipsoid 3a: 21.603 mm
numerical eccentricity of the ellipsoid 3a: 0.9761241
major semiaxis of the ellipsoid 3b: 34.93 mm
minor semiaxis of the ellipsoid 3b: 12.81 mm
numerical eccentricity of the ellipsoid 3b: 0.93032605
spacing of the outer focal points: 259.152 mm
radius of the spherical surface 33: 178.635 mm
radius of the spherical surface 38: 45.316 mm
radius of the inner spherical surfaces: 4.7315 mm
spacing of focal point 31 to spherical surface center point 34: 2.17 mm
spacing of focal point 36 to spherical surface center point 39: 0.45 mm
spacing of inner focal points 32, 37: 0.13 $\mu$m
center thickness of the ellipsoid 3a: 14.945 mm
center thickness of the ellipsoid 3b: 14.945 mm
aperture angle of the ellipsoid 3a: 4.16°
aperture angle of the ellipsoid 3b: 12.5°
material of the ellipsoids: Suprasil
material of the sphere: sapphire Objectives are illustrated in FIGS. 6a and 6b wherein both aspheric bodies are paraboloids. The axes 60' and 65' of the paraboloids 6a and 6b, respectively, are inclined to the optical axis 1 of the entire system. This affords the advantage that no inner aperture has to be masked out. The system has good imaging characteristics however, only for the imaging ratio 1:1. Furthermore, an even number of reflecting planar surfaces 62 (for a direct-vision objective) must be so arranged that the parallel bundle of rays crosses upon itself before the first and the last reflecting plane surface as, for example, at the location identified by reference numeral 6k. There then results an imagined wrapping of the path of the rays such that both parabolic outer surfaces 60 and 65 are axially symmetrically spaced with respect to each other and therefore function as an aplanatic system.

The paraboloids 6a and 6b are bounded on the entry end and exit end by spherical surfaces 63 and 68, respectively, having respective center points 64 and 69 coincident with corresponding ones of the focal points 61 and 66 of the paraboloids thereby defining the aplanatic surfaces for the focal points. The object plane is identified by reference numeral 6c and the image plane by 6d. The inner spherical surfaces 63' and 68' of the paraboloids have a radius of infinity or, stated otherwise, they are planar surfaces. These planar surfaces extend perpendicularly to the entering and exiting bundles of parallel light.

In FIG. 6a, a glass body 6e is arranged between the two planar surfaces 63' and 68'. The glass body 6e has reflecting planar surfaces provided with reflecting layers 62f. In lieu of the glass body 6e, it is of course possible to also provide two individual planar mirrors at the corresponding locations. This arrangement would, however, not lead to such a compact configuration as shown in FIG. 6a.

In FIG. 6b, a glass body 6g having four reflecting surfaces 62 is arranged between the two planar surfaces 63' and 68'. Because of the greater number of reflecting surfaces 62, the angle of incidence 69' of the rays reflected on surfaces 62 is so small that interference layers 6h can be effectively utilized there by means of which, for example, a smaller wavelength range is not reflected and is therefore not transmitted through the catoptric objective. An example of an application for such an objective will be described later in connection with FIG. 8b.

Figure 7:
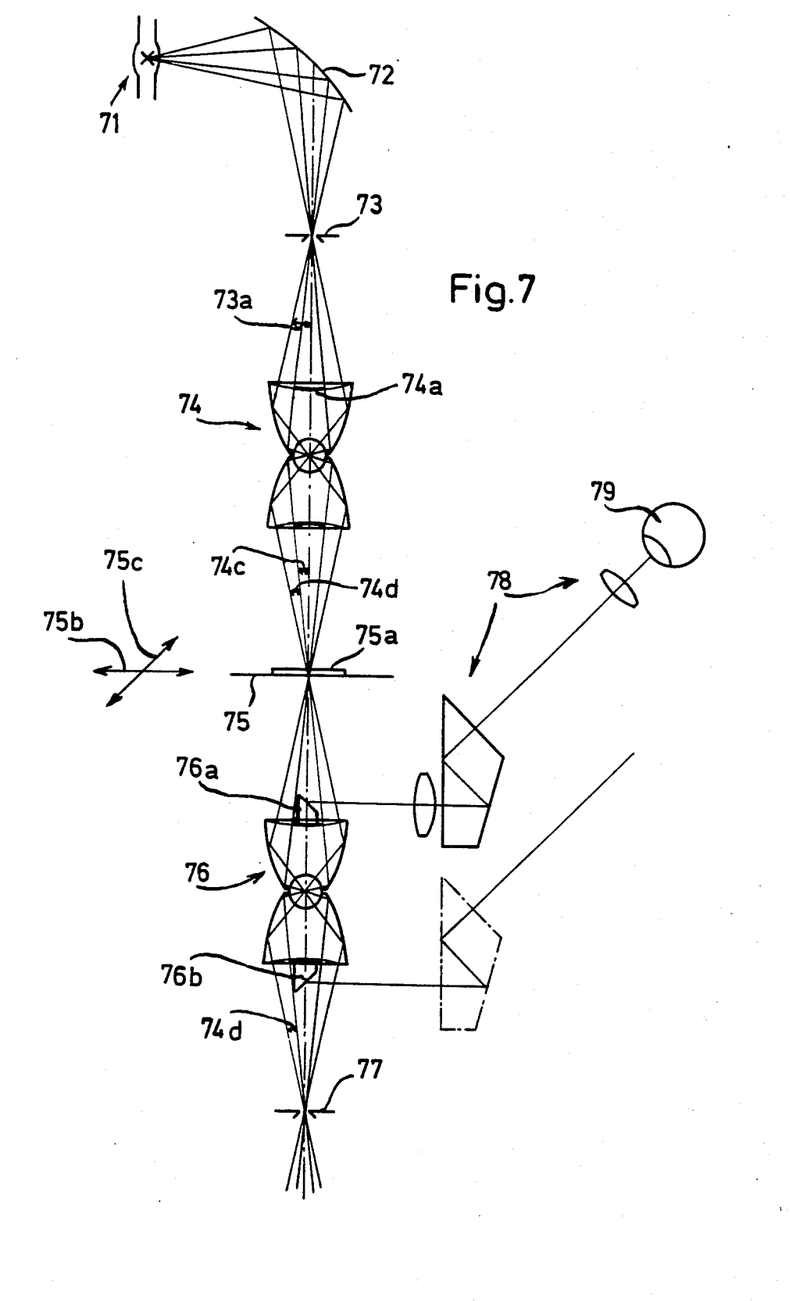
FIG. 7 is an example of the application of two objectives in the sample compartment of a spectrometer.

First an example of an application for the objective described with respect to FIG. 5c will be given and for which the precise data are delineated above. FIG. 7 shows two of such objectives in the sample compartment of a spectrometer. Reference numeral 71 identifies a light source which can be a xenon lamp which is imaged on the diaphragm 73 by means of the aspheric concave mirror 72. The diaphragm 73 can have, for example, a variable diameter of 25, 50 or 100 $\mu$m. This diaphragm 73 is imaged by the catoptric objective 74 in the sample plane 75 with a ratio of 1:1. The sample 75a can be shifted in the plane 75 in the direction 75b and 76c perpendicularly to the optical axis.

By means of a second catoptric objective 76, the sample plane 75 is imaged on the entry slit 77 of a diode-array spectrometer. This diode-array spectrometer has an aperture angle of 12.5° which is fully utilized because of the outer aperture 74d of the catoptric objectives 74 and 76 whereby only the small-area portion of the inner aperture 74c of the total aperture 73a is masked out by means of the required mask 74a.

Within the inner aperture 74c, glass cylinders 76a and 76b having reflective upper surfaces inclined at 45° to the optical axis are provided on the catoptric objective 76. By means of the glass cylinder 76a and 76b and with the aid of the observing arrangement 78, one can either observe which section of the sample 75a is in the path of the rays or control the illumination of the entry slit 77 of the spectrometer.

An advantage of the arrangement described compared to known combinations of microscope and photometer is not only that an entire spectrum can be taken up with substantially greater speed; instead, and above all, only that region of the sample is illuminated which must just then be measured and stray light from other areas of the sample is avoided.

Figures 8A, 8B:
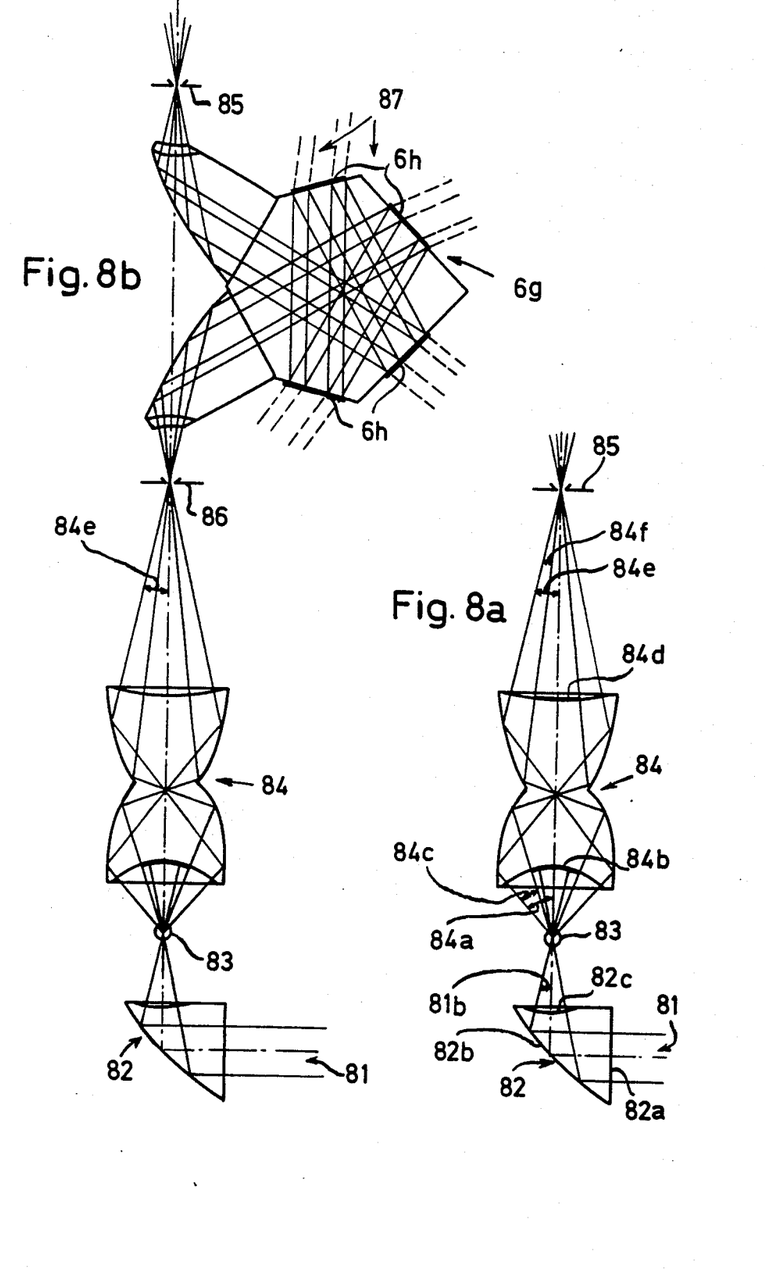

A further example of an application is illustrated in FIG. 8a wherein the path of the rays in the sample chamber of a fluorescence spectrometer is illustrated. In this fluorescence spectrometer, a large aperture utilized by the rays of the sample are reduced to the aperture of the spectrometer by means of a catoptric objective having two different ellipsoids. In FIG. 8a, reference numeral 81 identifies the rays of a laser (not shown) which are concentrated on the sample 83 with an aperture angle 81b from the optical element 82. The optical element 82 comprises a glass part with a planar entry surface 82a, a reflecting parabolic surface 82b and a spherically-shaped exit surface 82c. The focal point of the parabolic surface 82b and the center point of the spherically-shaped exit surface 82c lie at the center point of the sample 83.

On the other side of the sample 83, a catoptric objective 84 is so arranged that the outer focal point of the first ellipsoid lies in the center point of the sample 83 and therefore the mask 84b reflects the laser rays which were not absorbed by the sample 83 back into the sample, the mask 84b in this embodiment being configured as a mirror. The aperture angle 81b of the laser rays is selected to be smaller than that corresponding to the diameter of the mask or mirror 84b so that also the forwardly dispersed laser rays are intercepted by the mask 84b.

The objective 84 images the sample 83 on the entry slit 85 of the known diode-array spectrometer and thereby reduces the aperture angle 84a to the aperture angle 84e which is just as large as the aperture angle of the spectrometer whereby only the outer apertures 84c and 84f are utilized.

It is understood that it is also possible to adapt the aperture angle to that of a conventional spectrometer. For this purpose, only the objective must be dimensioned differently.

FIG. 8b shows the path of the rays of a Raman spectrometer which corresponds completely with the first part of the ray path shown in FIG. 8a for the fluorescence spectrometer. After the objective 84, it is not the entry slit which is in the image plane; rather, it is an intermediate diaphragm 86. This diaphragm 86 is imaged by means of the objective 87 onto the entry slit 85 of the diode-array spectrometer. The objective 87 is described above with reference to FIG. 6b. By means of the objective 87, the aperture angle 84e is of course not changed so that it is also in this instance optimally adapted to the spectrometer. The narrow band interference filter layers 6h have a very low reflection factor for the excitation wavelengths and a high transmittance factor; whereas, for the Raman spectrum which is to be investigated the filter layers 6h have a high reflection factor. Because of the four interference filter layers 6h which follow one upon the other, the excitation wavelength is very greatly reduced so that the light of these wavelengths exits from the glass body 6g; whereas, the useful light of the Raman spectrum is imaged with a high reflection factor on the entry slit 85 of the diode-array spectrometer.

It is understood that the foregoing description is that of the preferred embodiments of the invention and that various changes and modifications may be made thereto without departing from the spirit and scope of the invention as defined in the appended claims.

What is claimed is:

1. An objective comprising:
    a plurality of optically isotropic aspheric bodies defining a common optical axis and having respective aspherical outer surfaces and having respective first focal points on said axis;
    said aspherical outer surfaces defining respective uncoated reflecting surfaces;
    first spherical light passage surface means formed on a first one of said bodies and having a center point at least approximately in coincidence with the first focal point of said first body;
    second spherical light passage surface means formed on a second one of said bodies and having a center point at least approximately in coincidence with the first focal point of said second body;
    said bodies having respective second focal points also disposed on said axis and being at least approximately in coincidence with each other; and,
    one of said spherical light passage surface means being a light entry surface and the other one of spherical light passage surface means being a light exit surface.

2. The objective of claim 1, said bodies being configured as ellipsoids and said first focal points being outer focal points disposed on said optical axis; said second focal points being respective inner focal points disposed on said axis.

3. The objective of claim 2, said ellipsoids being directly connected with each other.

4. The objective of claim 2, said ellipsoids having mutually adjacent end faces configured to conjointly define a spherically-shaped air space therebetween having a center; said inner focal points being at least approximately in coincidence with said center.

5. An objective comprising:
    a plurality of optically isotropic aspheric bodies having respective aspherical outer surfaces and having respective focal points;
    said aspherical outer surfaces defining respective reflecting surfaces;
    first spherical light passage surface means formed on a first one of said bodies and having a center point at least approximately in coincidence with the focal point of said first body;
    second spherical light passage surface means formed on a second one of said bodies and having a center point at least approximately in coincidence with the focal point of said second body;
    one of said spherical light passage surface means being a light entry surface and the other one of spherical light passage surface means being a light exit surface;
    said bodies being configured as ellipsoids and said focal points being outer focal points disposed on an optical axis; said ellipsoids also having respective inner focal points also disposed on said axis and being at least approximately in coincidence with each other;
    said ellipsoids having mutually adjacent end faces configured to conjointly define a spherically-shaped cavity therebetween; and,
    a sphere made of optically isotropic material and disposed in said cavity, said sphere having a center at least approximately in coincidence with said two coincident inner focal points.

6. The objective of claim 5, the material of said sphere being selected so that the latter has a refractive index greater than the refractive index of said ellipsoids.

7. An objective comprising:
    a plurality of optically isotropic aspheric bodies defining a common optical axis and having respective aspherical outer surfaces;
    said aspherical outer surfaces defining respective uncoated reflecting surfaces;
    a first one of said bodies being a paraboloid having an inner focal point and a second one of said bodies being an ellipsoid having an inner focal point and an outer focal point on said axis;
    first spherical light passage surface means formed on said paraboloid and having a center point at infinity;
    second spherical light passage surface means formed on said ellipsoid and having a center point at least approximately in coincidence with said outer focal point of said ellipsoid;
    said inner focal points being in coincidence with each other and located on said axis;

one of said spherical light passage surface means being a light entry surface and the other one of spherical light passage surface means being a light exit surface;

said paraboloid and said ellipsoid having mutually adjacent end faces configured to conjointly define a spherically-shaped cavity therebetween; and, a sphere made of optically isotropic material and disposed in said cavity, said sphere having a center at least approximately in coincidence with said two coincident inner focal points.

8. The objective of claim 7, the material of said sphere being selected so that the latter has a refractive index greater than the refractive index of said paraboloid and said ellipsoid.

9. An objective comprising:

a plurality of optically isotropic aspheric bodies defining a common optical axis and having respective aspherical outer surfaces;

said aspherical outer surfaces defining respective uncoated reflecting surfaces;

said bodies being respective paraboloidal portions arranged with respect to said optical axis and having respective focal points on said optical axis;

said paraboloidal portions having respective axes inclined with respect to said optical axis and having respective outer spherical surfaces, said outer spherical surfaces defining respective center points coincident with corresponding ones of said focal points;

said paraboloidal portions having respective inner spherical surfaces; said inner spherical surfaces having respective center points at infinity; and, planar reflecting surface means arranged between said paraboloidal portions for conducting a parallel bundle of rays from the inner spherical reflecting surface of a first one of said paraboloidal portions to the inner reflective surface of a second one of said paraboloidal portions.

10. The objective of claim 9, said planar reflecting surface means being an even number of planar reflecting surfaces arranged so as to cause said bundle of rays to cross upon itself between the first one of said planar reflecting surfaces along the trace of said bundle of rays and the last one of said planar reflecting surfaces along said trace.

11. The objective of claim 10, comprising interference layer means covering at least a portion of said planar reflecting surfaces.

12. An objective for use with optical measuring instruments such as a spectrometer or the like comprising:

a plurality of optically isotropic aspheric bodies defining a common optical axis and having respective aspherical outer surfaces and having respective first focal points on said axis;

said aspherical outer surfaces defining respective uncoated reflecting surfaces;

first spherical light entry surface means formed on a first one of said bodies and having a center point at least approximately in coincidence with the first focal point of said first body;

second spherical light exit surface means formed on a second one of said bodies and having a center point at least approximately in coincidence with the first focal point of said second body; and, said bodies having respective second focal points also disposed on said axis and being at least approximately in coincidence with each other.

13. An objective comprising:

a plurality of optically isotropic aspheric bodies defining a common optical axis and having respective aspherical outer surfaces;

said aspherical outer surfaces defining respective uncoated reflecting surfaces;

a first one of said bodies being a paraboloid having an inner focal point and a second one of said bodies being an ellipsoid having an inner focal point and an outer focal point on said axis;

first spherical light passage surface means formed on said paraboloid and having a center point at infinity;

second spherical light passage surface means formed on said ellipsoid and having a center point at least approximately in coincidence with said outer focal point of said ellipsoid;

said inner focal points being in coincidence with each other and located on said axis; and, one of said spherical light passage surface means being a light entry surface and the other one of said spherical light passage surface means being a light exit surface.

14. The objective of claim 13, said paraboloid and said ellipsoid being directly connected with each other.

15. The objective of claim 13, said paraboloid and said ellipsoid having mutually adjacent end faces configured to conjointly define a spherically-shaped air space therebetween having a center; said inner focal points being at least approximately in coincidence with said center.

* * * * *